United States Patent
Behan et al.

(10) Patent No.: US 6,568,604 B1
(45) Date of Patent: May 27, 2003

(54) DISPENSING MEANS

(75) Inventors: John Martin Behan, Kent (GB); Keith Douglas Perring, Kent (GB)

(73) Assignee: Quest International BV, Naarden (NL)

( * ) Notice: Subject to any disclaimer, the term of this patent is extended or adjusted under 35 U.S.C. 154(b) by 0 days.

(21) Appl. No.: 09/647,555

(22) PCT Filed: Mar. 13, 1999

(86) PCT No.: PCT/GB99/00998

§ 371 (c)(1),
(2), (4) Date: Oct. 2, 2000

(87) PCT Pub. No.: WO99/49904

PCT Pub. Date: Oct. 7, 1999

(30) Foreign Application Priority Data

Apr. 1, 1998 (EP) .............................. 98302568

(51) Int. Cl.[7] .................................. B05B 7/26
(52) U.S. Cl. .................. 239/314; 239/315; 239/316; 239/318; 239/305; 239/346
(58) Field of Search ................. 239/303–307, 239/310, 314–316, 318, 346, 349

(56) References Cited

U.S. PATENT DOCUMENTS

| | | | | |
|---|---|---|---|---|
| 557,878 A | * | 4/1896 | Pownall | 239/305 |
| 2,228,922 A | * | 1/1941 | Gorlick | 239/310 |
| 2,993,652 A | * | 7/1961 | Curry | 239/310 |
| 3,300,095 A | * | 1/1967 | Marraffino | 222/146.3 |
| 3,338,479 A | * | 8/1967 | Marraffino | 222/129 |
| 3,370,756 A | * | 2/1968 | McKinnie | 222/146.3 |
| 4,240,418 A | | 12/1980 | Rosskamp et al. | |
| 4,396,152 A | | 8/1983 | Abplanalp | |
| 5,490,630 A | | 2/1996 | Hecker | |

FOREIGN PATENT DOCUMENTS

| | | |
|---|---|---|
| WO | WO 96/42001 | 12/1996 |
| WO | WO 97/25662 | 7/1997 |

* cited by examiner

*Primary Examiner*—Christopher Kim
(74) *Attorney, Agent, or Firm*—Morgan, Lewis & Bockius LLP

(57) ABSTRACT

A device for dispensing a liquid in a carrier fluid flow comprises a container (10) for the liquid, into which a pressure flow of carrier fluid is driven. A liquid conduit (20) within the container has an outlet (22) in the path of the carrier fluid flow into the container so that liquid is taken up and is carried with the flow, through an outlet (26) from the container. The container can be formed by a disposable capsule that is replaceably inserted into the device.

7 Claims, 3 Drawing Sheets

DISPENSING MEANS

Figure 1:
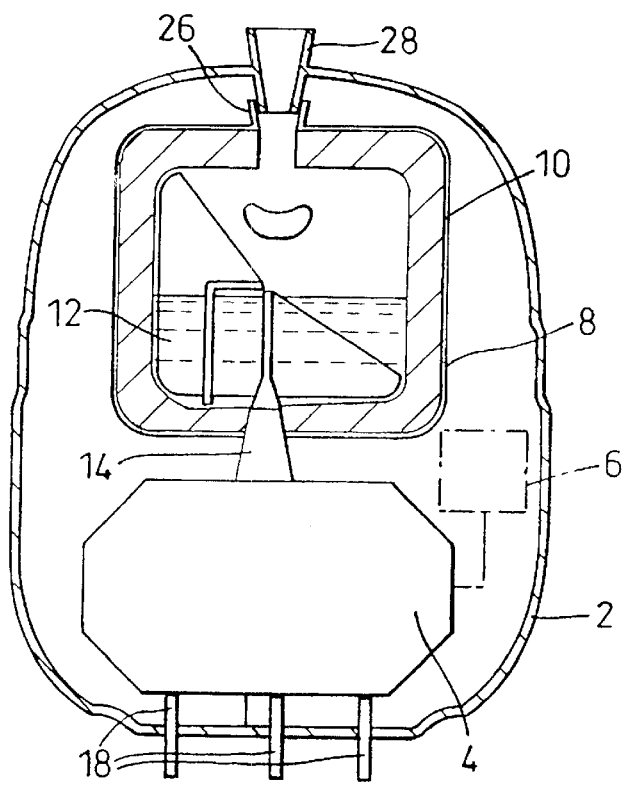

This application is the national phase of international application PCT/GB99/00998 filed Mar. 31, 1999 which designated the U.S.

This invention relates to devices for the dispensing of liquids into a carrier fluid. While the invention is applicable to the release of all kinds of active materials into a liquid or gaseous carrier fluid, it is particularly concerned with the dispersal of liquids for scenting the fluid or for freshening the surrounding atmosphere.

It is known to deliver materials, in particular liquids, into the surrounding atmosphere in a variety of ways, for such purposes as freshening or perfuming the air. For example, aerosol sprays are used, but they have a tendency to produce large droplets of the liquid which, because of their weight, do not travel far from the spray zone. Furthermore, the carrier gases used in aerosols may be environmentally harmful.

Fragranced gels are also used as a static source for the delivery of volatile substances into the atmosphere. They operate continuously, which is not always required, however, and their effectiveness decreases with time. They also have the disadvantage that it is not usually possible to vary the intensity of delivery.

Electrically heated devices and candles are other known means which use heat to release fragrances into the atmosphere. The materials to be dispersed must be stable at the elevated temperatures experienced and this sets severe constraints, in particular on the type of fragrances which can be used.

In one aspect of the present invention, a dispensing device is provided to disperse a liquid into a carrier fluid flow, the device comprising a container for the liquid, a carrier fluid entry conduit opening into the container for directing a pressure flow into the container, an outlet from the container for said fluid, a conduit for the liquid within the container having an outlet in the influence of the flow through said carrier fluid conduit whereby said flow takes up liquid from the liquid conduit to disperse it in the carrier fluid flow.

The device may be provided with its own carrier fluid pumping means so as to operate as a self-contained unit. It is also possible, however, for the device to form an auxiliary unit which can cooperate with other apparatus producing the carrier fluid flow. For example, a device according to the invention can be arranged to be actuated by the air flow from the vacuum cleaner, or a ventilating fan, or by steam as from a humidifier, or from a water flow as in the piped water supply to a bath or a shower or a water closet.

The conduit may take the form of one or more capillary passages, so that liquid can be drawn by capillary action towards the conduit outlet to be available substantially instantaneously on start-up. The capillary action can also reduce any loss of the liquid from the container during periods when the carrier fluid does not flow through it.

In one form of the device, intended to dispense a liquid into a gaseous carrier fluid such as a flow of air, the carrier fluid entry conduit terminates in an upper region of the container, above the level of the liquid to be dispensed, and the liquid conduit extends from a bottom region of the container, to said entry conduit termination above the liquid level.

The device may comprise means for capturing larger droplets entrained in the gaseous flow so that the flow leaving the device contains the liquid in the form of a fine aerosol or a vapour, in which the average size of the particles may be not be substantially greater than, for example, 10 microns, to delay precipitation from the air flow. Because the dispersal of the liquid is effected by the forced gaseous flow from the device, it is possible to control the rate of dispersal, so permitting large spaces to be treated rapidly and allowing the dispensing of the liquid to be stopped rapidly if so required.

It is sometimes desirable to be able to vary the material being dispensed. Although this can be done easily with passive dispensing devices, such as containers from which the material, eg. in a fragranced gel, is dispensed simply by exposure to the atmosphere when the container is opened, it is more troublesome to make the change with an active dispensing device such as the electrically heated device referred to earlier, where the material in the device must be replaced.

According to another aspect of the invention, a liquid dispensing device is provided comprising a carrier fluid inlet for communication with a plurality of carrier fluid entry conduits arranged in parallel and opening into respective containers for liquids to be dispensed into the carrier fluid, within each container a conduit for the liquid having an outlet in the influence of a carrier fluid flow through the associated entry conduit for dispersing the liquid into said flow, and an outlet for said flow carrying the liquid dispensed, means being provided for directing the carrier fluid through said entry conduits selectively.

Thus, in contrast to known air freshening devices which are able to provide only a single fragrance, or which require cumbersome and time-consuming manipulation to change the fragrance to be dispensed, it is possible to choose an alternative fragrance in a simple and almost instantaneous manner.

The means for selection may be arranged to allow the carrier fluid flow to be directed to two or more containers at a time, so that the user is able to dispense combinations of the fragrances available if desired.

In a further aspect of the invention, a liquid dispensing device is provided comprising means for generating a carrier fluid flow, a replaceable capsule removably connected to a fluid flow exit from said generating means, said capsule forming a container for the liquid to be dispensed and comprising means for dispensing the liquid into the flow from said exit, the capsule having an outlet for directing the flow carrying the liquid to the exterior.

Employing a removable capsule as the liquid container it is possible to provide a device which can be set up and operated in a particularly simple manner. Preferably, the capsule has fluid-tight seals on said outlet for the combined flows and on an inlet, and means are provided in the device for breaking said seals upon insertion of the capsule into the device.

The capsule can be formed with respective passages for the liquid to be dispensed and for the flow from the generating means, the liquid passage having an outlet end disposed in the region of said carrier fluid flow into which the liquid is drawn by venturi or jet pump action. Conveniently, the liquid passage is formed by one or more capillary conduits.

In an arrangement of a device according to the invention having means for dispensing liquid from alternative containers, the containers can be provided in the form of disposable sealed capsules, so that replacement of a capsule provides a ready means of changing the liquid to be dispensed. The use of the device can be further simplified if a set of capsules for the respective fluid entry conduits is provided as a single unit.

It will be understood that if devices according to the invention are arranged to be operated with disposable capsules of the liquid to be dispensed, they may be supplied, at least initially, without capsules which would be obtainable separately by the user.

According to yet another aspect of the invention, a liquid-containing capsule is provided for a liquid dispensing device, the capsule comprising an inlet conduit for admitting a flow of carrier fluid into the capsule interior, a conduit for the liquid to be dispensed, preferably comprising at least one capillary passage, having an exit opening exposed to said carrier fluid flow within the capsule for the dispersal of the liquid into said flow, and an outlet opening for the carrier fluid flow carrying the dispersed liquid.

When operating with a forced gaseous flow as the carrier fluid, it can be conveniently arranged that the liquid conduit projects upwardly above the level of the liquid in the capsule to adjacent an opening through which the carrier fluid enters the interior space of the capsule in an upper region, above the top of the liquid in the capsule. The liquid to be dispensed may be arranged to be drawn into the carrier fluid flow generating a reduced ambient pressure in the region of the exit from the liquid conduit, as by venturi or jet pump action.

In one preferred form, the capsule also has a barrier member located in a direct path between said conduit exit and the outlet opening, so as to deflect the carrier fluid flowing towards the exit. Larger droplets of liquid entrained in the flow will impinge on the barrier member and fall back into the main body of liquid the remaining, more intensely dispersed liquid in the flow from the capsule being carried further from the capsule as the flow dissipates into the surrounding atmosphere.

In a preferred construction, the capsule has a body formed by a pair of wall members sandwiched together to define an interior space within which the liquid is held. It is also preferred to form the liquid conduit on an internal member which is inserted into the body of the capsule. The internal member may comprise means locatable on said inlet conduit in order to ensure the liquid conduit outlet is held in close proximity to the outlet from the carrier fluid conduit.

Figure 2:
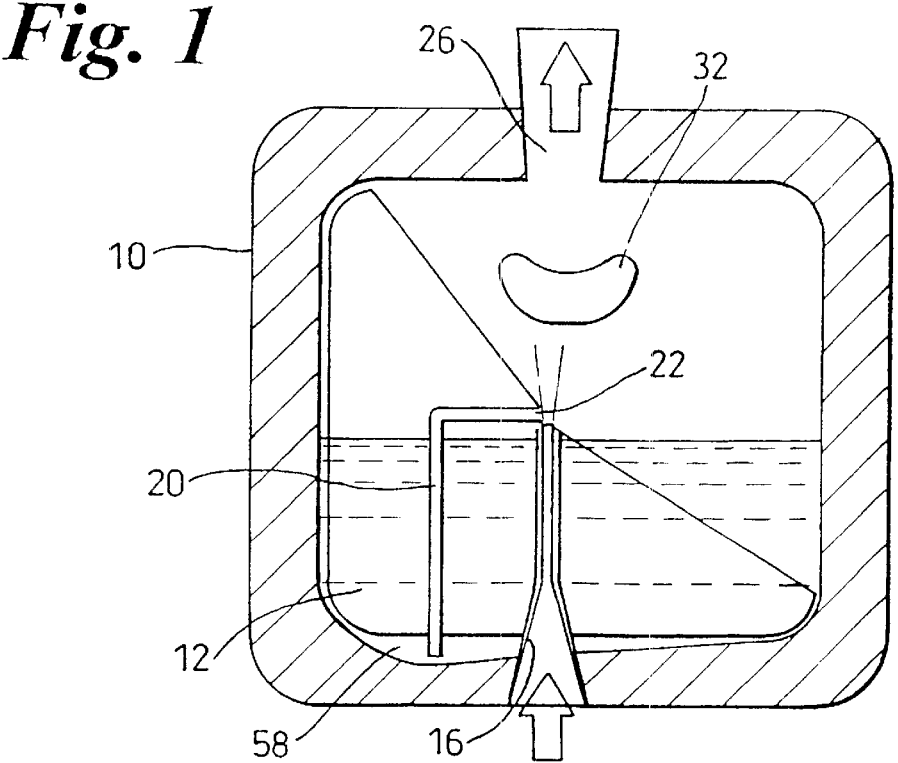
Figure 3:
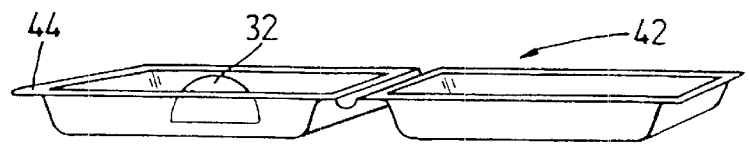
Figure 4:
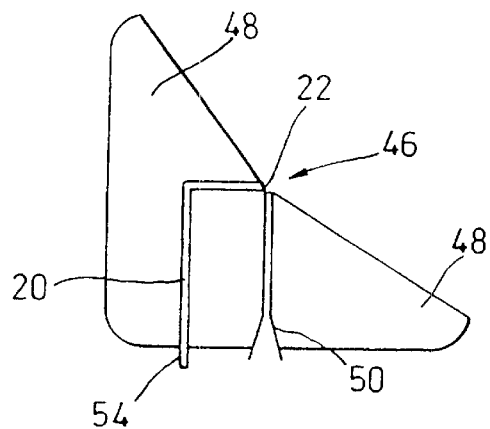
Figure 5:
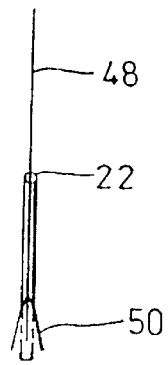
Figure 6:
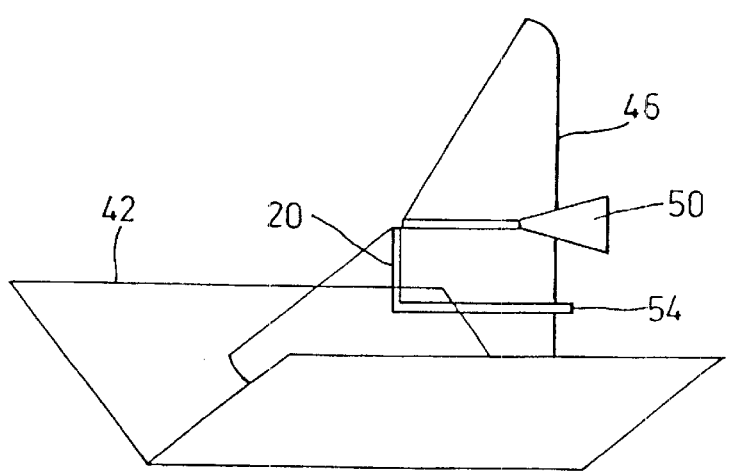
Figure 7:
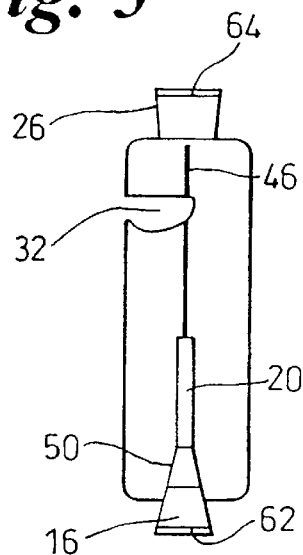
Figure 8:
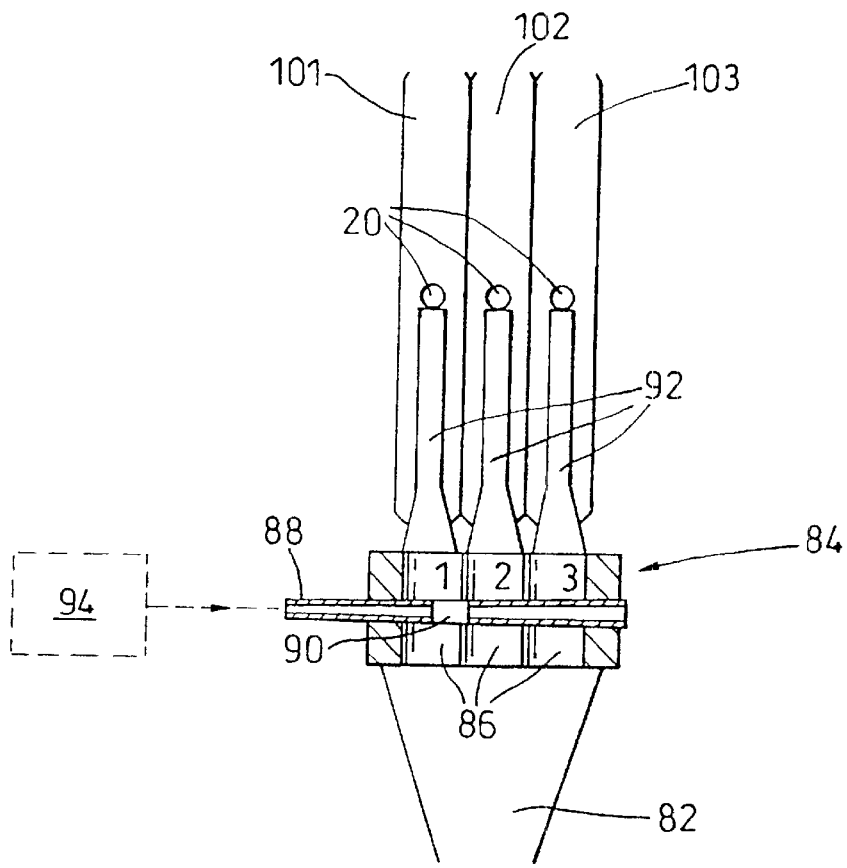
Figure 9:
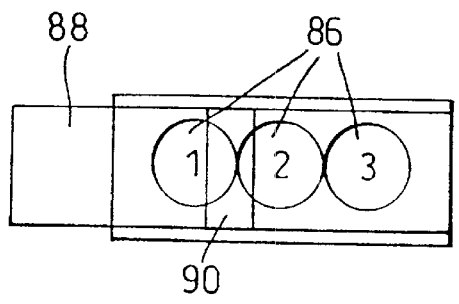
Figure 10:
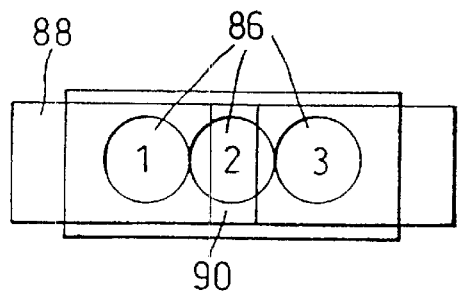

The invention will be further described by way of example with reference to the accompanying schematic drawings, in which:

FIG. 1 is an illustration of a dispensing device according to the invention,

FIG. 2 is an illustration to a larger scale of a capsule according to the invention for the device of FIG. 1, FIG. 3 shows the capsule body moulding, FIGS. 4 and 5 are front and side views of the capsule insert, FIG. 6 illustrates the assembling together of the capsule body and insert, FIG. 7 is a sectional side view of the capsule, FIG. 8 illustrates a part of another dispensing device according to the invention which allows alternative liquids to be dispensed selectively, and FIGS. 9 and 10 are plan views of the selector valve of the device of FIG. 8 in alternative positions.

In the device illustrated in FIGS. 1 to 7, a housing 2, indicated merely diagrammatically, contains an air pump 4, a timer 6 for controlling the pump and a receiving space 8 in which is inserted a disposable capsule 10 containing a liquid 12, such as a fragrance, to be dispensed. The pump has a delivery nozzle 14 projecting upwardly into the receiving space 8. Within the capsule, a sleeve 16 (FIG. 2) of similar form to the delivery nozzle 14 projects upwards from the bottom of the capsule to above the level of the liquid 12, and when the capsule is mounted in the receiving space as shown, the air delivery nozzle is plugged into the sleeve.

The housing 2, with the pump 4 and timer 6 forms a self-contained electrical unit with terminals 18 for connection to an external power source, or it can be battery-driven.

In the interior of the capsule 10 a conduit 20 extends from close to its bottom edge to an exit opening 22 above the level of the liquid, immediately adjacent the upper, open end of the sleeve 16. In this example, the conduit 20 is formed as a capillary tube to draw liquid to the exit opening. When air is pumped through the nozzle 14, the static pressure at the outlet from the conduit is lowered in the manner of a venturi or jet pump device. Liquid at the conduit exit is immediately entrained in the air flow and is carried in the air flow, in the form of fine droplets or a vapour. Through a top outlet nozzle 26 of the capsule into which fits diffuser nozzle 28 formed on the housing 2, the flow of air and atomised liquid is dispersed into the outside atmosphere. Capillary action, and the reduced ambient pressure at the exit from the conduit 20, maintains the flow of liquid through the conduit while air is being pumped through the capsule.

A diverter tongue 32 is located in the capsule interior above the air delivery nozzle, imposing a deviation on the path of the flow to the outlet nozzle 26. Larger drops of liquid that may be drawn into the air flow will impinge on the tongue 32 and fall back into the main body of the liquid, so ensuring that liquid in the flow through the outlet nozzle has been reduced to aerosol size droplets, preferably not significantly greater than 5–10 microns in size, which will remain suspended longer in the air flow.

Under the control of the timer 6, which can be adjusted by the user, liquid is thus dispersed into the atmosphere at a required rate. In each operation of the pump, the forced air flow and fine droplet size of the liquid carried in it allow rapid dispersal of the liquid through a relatively large space.

In an unillustrated modification of the above-described device, the timer is supplemented with or replaced by a detector such as a passive infra-red detector to sense movement within the space being treated. The device will not operate therefore when the space is unoccupied. Because the dispersal of the liquid can be achieved very rapidly, it is possible to employ this measure to economise on the consumption of the liquid without any significant lessening of the effect of the device.

While the device of FIG. 1 is in the form of a plug-in unit that can be connected independently to a power supply through an electrical plug socket (not shown), a dispensing device according to the invention can also form part of a larger apparatus, in which the air pump is itself an air-circulating fan, for example the air flow being produced in an air conditioning unit or a passenger vehicle ventilation system. Moreover, when the dispensing device is arranged as an independent unit, the air flow can be generated in other ways, such as by mechanical means or by aerosols. For example, it may be convenient for a hand-held form of the device to be manually operated, or to have a dispensing device which is operated by the movement of a door or other object. It will be understood without further illustration how known forms of mechanically operated pumps or bellows can be substituted for the electrical air pump 4 shown in FIG. 1.

The capsule 10 may be formed as a disposable unit to be readily replaceable when the liquid has been exhausted. In the example, illustrated, the capsule main body 42 is vacuum-formed or molded and comprises a pair of dished parts joined by an integral hinge defining one edge of the capsule. Planar rims 44 on the dished parts are sealed against each other, when the two parts are folded together, to form the liquid-containing interior space. One of the dished parts is integrally formed with a depression that provides the diverter tongue 32. The entry nozzle sleeve 16 and the outlet nozzle 26 are integrally formed in the body molding.

The liquid supply conduit 20 is formed in an insert 46 comprising planar wings 48 that extend into diagonally opposite corners of the generally rectangular interior of the capsule, so locating the insert in place within the capsule. The insert 46 is further located relative to the air delivery nozzle 14 by an integrally molded outer sleeve 50 which fits telescopically over the entry nozzle sleeve 16 of the body molding. The capillary tube providing the liquid conduit 20 is integrally molded in the insert 46. It has an entry end 54 projecting below the bottom edge of the main planar part of the insert and the exit opening 22 is located immediately adjacent the upper end of the outer sleeve 50.

At the bottom of the capsule, the rims 44 have an inclined inner edge forming a depression 58 (FIG. 2) into which the entry end 54 of the conduit 20 extends. The liquid in the capsule can thereby be virtually completely exhausted before the flow through the tube is interrupted.

In the manufacture of the capsule, the body 42 and insert 46 are assembled together and the capsule is closed by sealing together the peripheral rims 44 of the body. One or both of 42, 46 is formed with a sealing membrane (not shown) closing off the path through the entry nozzle sleeve 16 into the capsule interior or a seal is applied to this passage, as indicated at 62 in FIG. 7 before the next stage of manufacture in which the liquid is inserted into the capsule through the open outlet nozzle 26, to fill the capsule almost to the height of the entry nozzle sleeve 16. The outlet nozzle 26 is then sealed as indicated at 64 in FIG. 7.

When the capsule is inserted into the device, the pump delivery nozzle 14 breaks the seal 62 on the entry nozzle sleeve 16 of the capsule body. The seal 64 on the outlet nozzle is also ruptured, possibly by a further piercing element (not shown) in the housing 2 to make the device ready for use.

FIGS. 8 to 10 illustrate a further development of the device described above in which liquid can be dispensed selectively from a number of alternative capsules in an analogous manner 6 that are already described with reference to FIGS. 1 and 2. FIG. 8 shows three such capsules, 101,102,103, each of the same form as the capsule 10 described above.

The device is shown only fragmentarily but FIG. 8 indicates a main air outlet 82 from an air pump (not shown) or other air flow source forming a plenum chamber at the entry side of a slide valve 84 comprising a housing with three parallel passages 86 leading from the outlet 82. A valve member 88 having an aperture 90 is slidable in the housing to align the aperture with one or more of the passages 86. Projecting from the exit side of the valve, in alignment with the passages 86, are respective air delivery nozzles 92. The capsules 101,102,103 are mounted on the nozzles 92 in the same manner as the capsule of the example in FIGS. 1 and 2 is mounted on the pump delivery nozzle 14 (for simplicity the capsule sleeves fitting the nozzles are not shown), with their liquid conduits 20 extending close to the outlet ends of the nozzles 92. In particular applications it may be preferred to form the capsules 101,102,103 as a composite unit, so that they can be replaced in a single operation.

When air is blown through the air outlet 82, whether from an integral air pump in the device as in the example of FIG. 1, or whether from an external source as in the example of an air conditioning system mentioned above, liquid will be taken up from the capsule or capsules to which the air is admitted by the slide valve 84. Thus, with the valve in the position shown in FIG. 9, the air flow is divided between the capsules 101 and 102, while in the position shown in FIG. 10, the valve admits air only to the capsule 102.

The valve 84 can be manually operated, and it will be clear that it then provides the user with a simple and virtually instantaneous control over the material to be dispensed. As is indicated only schematically at 94, the valve may alternatively be automatically operated, for example, being driven by a cam or other mechanism coupled to the air pump or driving motor, or by a timer. The drive 94 may displace the valve member in a continuous or stepped manner. Automatic operation gives the advantage, if the capsules contain alternative fragrances, that by varying continually the fragrances being dispensed into the atmosphere it is possible to counter the desensitising effect of fragrance fatigue which can occur through exposure to a single fragrance over a period of time.

It has already been indicated that devices according to the invention can be incorporated in apparatus in which a fluid flow is generated, using that fluid as a carrier for the liquid to be dispensed from the device. As further examples that need no additional illustration, it is possible in this manner to dispense fragrances and/or germicidal substances in the flow of air through a vacuum cleaner or in a flow of steam through a humidifier or in the flow of water into a bath or shower or in the flushing flow of a water closet. In effect an arrangement such as that shown in FIG. 8, whether with a single capsule or multiple capsules, with the carrier flow arriving via the outlet 82, would achieve these purposes.

In a further application of the invention, the liquid in a container provides a carrier into which the liquid of the device is dispensed. The dispensing device then forms a part of or an attachment to the main container. One example of this application of the invention, for which FIG. 8 also serves as an illustration, is as a means for dispensing a fragrance into a bleach, where it may be required to leave the two liquids unmixed until the last moment to minimise the oxidising action of the bleach on the fragrance.

What is claimed is:

1. A liquid dispensing device comprising means for generating a carrier fluid flow, said generating means including an exit for said carrier fluid flow, a replaceable capsule removably connected to said carrier fluid flow exit of said generating means, said capsule forming a container for a liquid to be dispensed and comprising means for dispensing the liquid into the carrier fluid flow received into said capsule from said exit, said dispensing means comprising respective passages for the liquid to be dispensed and for the carrier fluid flow from the generating means, the passage for said liquid having an inlet end adjacent a base of the container and an outlet end disposed in the region of said carrier fluid flow into which the liquid is drawn by action selected from venturi action and jet pump action, the capsule having an outlet for directing the carrier fluid flow carrying the liquid out of said dispensing device, said capsule having fluid-tight seals on said outlet and on an inlet for the carrier fluid flow from the exit of said generating means, and means in the device for breaking at least one of said seals upon insertion of the capsule into the device.

2. A device according to claim 1 wherein said means for generating a carrier fluid flow is a gaseous fluid pump for generating the carrier fluid flow, and wherein said dispensing means are arranged to dispense liquid in said container in droplet or vapour form into gaseous carrier fluid flow from the pump.

3. A device according to claim 1 wherein the passage for said liquid comprises a capillary tube.

4. A device according to claim 1 wherein said generating means comprises one or more additional fluid flow exits and the device comprises a corresponding number of additional replaceable capsules removably connected to respective said fluid flow exits, and means for directing the fluid flow through said exits selectively.

5. A liquid-containing capsule for use in a device for dispensing a liquid from the capsule into a carrier fluid flow, the capsule comprising a body enclosing a space for the liquid, an inlet conduit for admitting a flow of the carrier fluid into said capsule, a conduit for the liquid to be dispensed having an exit opening exposed to said carrier fluid flow within the capsule for the dispersal of the liquid into said flow, and an outlet opening for the flow of carrier fluid flow from the capsule carrying the dispersed liquid, the exit opening of the conduit for said liquid being so arranged that liquid is dispersed into the carrier fluid flow from the exit of said liquid conduit by action selected from venturi action and jet pump action, said liquid conduit comprising at least one capillary passage extending from a bottom region of the capsule, and the capsule having rupturable fluid-tight seals on said inlet conduit and said outlet opening.

6. A capsule according to claim 5 comprising an insert within said body having the liquid conduit integrally formed therewith.

7. A capsule according to claim 6 wherein the outer body is formed by a pair of members sandwiched together to define said space.

* * * * *